(12) United States Patent
Sato et al.

(10) Patent No.: US 7,337,662 B2
(45) Date of Patent: Mar. 4, 2008

(54) ELECTROSTATIC CAPACITY TYPE LIQUID STATE DETECTING SENSOR

(75) Inventors: Yoshikuni Sato, Nagoya (JP); Takashi Yamamoto, Aichi (JP); Takeo Sasanuma, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 111 days.

(21) Appl. No.: 11/136,649

(22) Filed: May 25, 2005

(65) Prior Publication Data

US 2005/0285608 A1    Dec. 29, 2005

(30) Foreign Application Priority Data

Jun. 24, 2004  (JP)  .............................. 2004-186042

(51) Int. Cl.
*G01F 23/26* (2006.01)
(52) U.S. Cl. .................................................. 73/304 C
(58) Field of Classification Search .............. 73/304 C; 361/284; 340/450, 612, 620
See application file for complete search history.

(56) References Cited

U.S. PATENT DOCUMENTS

| | | | | |
|---|---|---|---|---|
| 2,375,084 A | * | 5/1945 | Coroniti et al. | ........... 73/304 C |
| 3,214,655 A | * | 10/1965 | Di Giacomo | ................ 361/284 |
| 4,051,431 A | | 9/1977 | Wurster | ........................ 73/861 |
| 5,543,722 A | | 8/1996 | Suzuki et al. | ............. 166/254.2 |
| 2003/0010494 A1 | | 1/2003 | Bose et al. | .................. 324/675 |

FOREIGN PATENT DOCUMENTS

| EP | 0 341 675 A2 | 11/1989 |
|---|---|---|
| JP | 7-318395 | 12/1995 |
| JP | 8-296932 | 11/1996 |
| JP | 2002-277427 | 9/2002 |
| JP | 2003-57093 | 2/2003 |

OTHER PUBLICATIONS

Wah On Ho et al.; "Electrochemical Sensor for Measurement of Urea and Creatinine in Serum Based on ac Impedance Measurement of Enzyme-Catalyzed Polymer Transformation"; Analytical Chemistry, Vo. 71, No. 10, May 15, 1999, pp. 1940-1946.

* cited by examiner

*Primary Examiner*—Hezron Williams
*Assistant Examiner*—Rodney Frank
(74) *Attorney, Agent, or Firm*—Sughrue Mion, PLLC (57) ABSTRACT

An electrostatic capacity type liquid state detecting sensor includes an outer tubular electrode, and an inner electrode disposed within the outer tubular electrode and having an insulation layer at an outer surface portion to be brought into contact with liquid contained in a container for detection of a state of the liquid, wherein the thickness of the insulation layer is less than 500 µm and not less than 100 µm.

14 Claims, 6 Drawing Sheets

ELECTROSTATIC CAPACITY TYPE LIQUID STATE DETECTING SENSOR

BACKGROUND OF THE INVENTION

The present invention relates to an electrostatic capacity type liquid state detecting sensor for detecting a state of liquid contained in a container.

The exhaust gases emitted from a diesel vehicle contain nitride oxides (NOx) other than carbon monoxide (CO) and hydrocarbon (HC). In recent years, it has been practiced to reduce the harmful nitride oxides into non-harmful gas. For example, it has been proposed to dispose at the exhaust muffler of the diesel vehicle an NOx selective reduction (SCR) catalyst, while keeping urea water that serves as reduction agent in a container separately installed on the vehicle, and inject the urea water into the catalyst to thereby reduce NOx into a non-harmful gas such as $N_2$. With this system, if the urea water is used up, it becomes impossible to urge NOx to be reduced so that a large amount of NOx is emitted from the vehicle. To solve this problem, there have been proposed various steps such as a step of disposing a sensor in a container containing urea water for detecting the level of the urea water and giving the alarm when the remaining amount of the urea water becomes lower than a predetermined value.

As an example of such a sensor for detecting a water level, there is known an electrostatic capacity type liquid state detecting sensor. The electrostatic capacity type liquid state detecting sensor detects an electrostatic capacity at an intervening space between an outer tubular electrode made of a conductive material and in the form of a thin, long tube and an inner electrode disposed within the outer tubular electrode so as to extend axially therewithin. In case of the electrostatic type liquid level detecting sensor used for measuring the level of the liquid that is electrically conductive as urea water, the inner electrode is formed with an insulation layer on the outer surface with a view to preventing occurrence of a short between the outer tubular electrode and the inner electrode. The electrostatic capacity type liquid state detecting sensor is set in a container so that the axis of the outer tubular electrode extends vertically, i.e., upward and downward of the water level. In case the liquid is electrically conductive, the electrostatic capacity of a sensor portion not dipped in the liquid is determined depending upon an air layer in an intervening space between the outer tubular electrode and the inner electrode and the thickness of the insulating layer of the inner electrode. On the other hand, the electrostatic capacity of a sensor portion dipped in the liquid is determined depending upon the thickness of the insulating layer, since the electrically conductive liquid becomes equal in potential to the outer tubular electrode, and becomes higher in electrostatic capacity than that of the sensor portion not dipped in the liquid. For this reason, as the sensor portion dipped in the liquid increases, the measured electrostatic capacity increases, thus making it possible to detect a variation of the water level.

In case of measurement of the liquid level by means of such an electrostatic capacity type liquid state detecting sensor, if the intervening space is constant, the liquid level and the electrostatic capacity are proportional to each other. Namely, the more uniform the thickness of the insulation layer formed on the outer surface of the inner electrode becomes, the more accurate the detection of the sensor becomes. In the conventional electrostatic capacity type liquid state detecting sensor, the insulation layer is formed by a resin tube that covers the outer surface of the inner electrode such that the insulation layer is uniform in thickness.

SUMMARY OF THE INVENTION

In the meantime, in order to prevent breakage of the resin tube during the process of covering the inner electrode by the resin tube and during the process of assembling the outer tubular electrode and the inner electrode coaxially with each other, it is necessitated to increase the thickness of the resin tube and thereby keep the strength of the resin tube above a certain value. However, the electrostatic capacity depending upon the thickness of the insulation layer decreases with increase of the thickness of the insulation layer. Thus, in case an inner electrode formed with an insulation layer by using a resin tube of a relatively large thickness, the range of the electrostatic capacity that can be detected by the sensor becomes narrower. In case the range of detectable electrostatic capacity is narrower, it is inevitable to utilize electronic parts having a high accuracy in order to improve the detection accuracy of the sensor, thus causing a problem that the sensor unit including a detection circuit becomes expensive. Further, the rate of the floating capacity caused by the circuit structure such as a wiring pattern of the sensor to the detectable electrostatic capacity becomes larger, so that the floating capacity cannot be ignored as noise, thus causing a problem that the detection accuracy of the sensor is lowered.

On the other hand, it is considered to make thinner the insulation layer with a view to increasing the range of detectable electrostatic capacity. However, if the insulation layer is made thinner, there is a possibility that the insulation layer is easily broken by a small impact applied thereto from the outside during transfer or the like in the production process and therefore it becomes impossible to attain suitable measurement of the electrostatic capacity and therefore suitable detection of the liquid state.

It is accordingly an object of the present invention to provide an electrostatic capacity type liquid state detecting sensor that can detect the liquid state accurately by determining a thickness of an insulation layer formed on the outer surface of the inner electrode so as to be included within predetermined limits.

To achieve the above object, there is provided according to an aspect of the present invention an electrostatic capacity type liquid state detecting sensor comprising an outer tubular electrode, and an inner electrode disposed within the outer tubular electrode and having an insulation layer at an outer surface portion to be brought into contact with liquid contained in a container for detection of a state of the liquid, wherein the thickness of the insulation layer is less than 500 μm and not less than 100 μm.

According to the electrostatic capacity type liquid state detecting sensor, the thickness of the insulation layer formed at a surface portion of the inner electrode to be brought into contact with liquid is determined to be not less than 150 μm. Thus, as will be supported by the result of evaluation test which will be described later, it becomes possible to prevent the insulation layer from being broken to expose the outer surface of the inner electrode. Accordingly, it becomes possible to prevent the insulation layer from being broken or damaged at the time of assembly of the sensor. Further, the electrostatic capacity to be measured by the sensor depends on the thickness of the insulation layer. Since the thickness of the insulation layer is limited to be less than 500 μm, the maximum value of the electrostatic capacity to be measured can be maintained relatively high. Namely, the range of electrostatic capacity to be measured becomes relatively wide and therefore detection of the liquid level can be attained by a relatively inexpensive circuit structure without using a circuit having a high resolving power (capable of detecting a fine electrostatic capacity difference). Further, the electrostatic capacity to be measure can be sufficiently large with respect to the floating capacity caused by a circuit, or the like, thus making it possible to prevent the detection accuracy of the sensor from being lowered. In the meantime, the insulation layer with the above-described thickness limits can be formed by a resin tube or by resin coating. However, it is preferable to form the insulation layer by resin coating from the point of view of attaining the above-described thickness limits while attaining a high adherence of the insulation layer to the outer surface of the inner electrode.

In the meantime, the thickness of the insulation layer formed on the outer surface of the inner electrode is preferably less than 500 μm and not less than 150 μm. By determining the thickness of the insulation layer to be not less than 150 μm, as will be supported by the result of evaluation test which will be described later, it becomes possible to effectively prevent the insulation layer from being broken to expose the outer surface of the inner electrode. Accordingly, it becomes possible to effectively prevent the insulation layer from being broken or damaged at the time of assembly of the sensor, and it becomes possible to make the yielding rate closer to 100%.

Further, in the above-described electrostatic capacity type liquid state detecting sensor wherein the inner electrode is in the form of a hollow or solid cylinder, it is preferable that the difference in thickness between a thickest portion and a thinnest portion of the insulation layer is 300 μm or less with respect to a section crossing the axis of the inner electrode, i.e., when observed in cross section.

Since in the electrostatic capacity type liquid state detecting sensor according to the present invention, the difference in the thickness between a thickest portion and a thinnest portion of the insulation layer is determined to be 300 μm or less when observed in cross section, the circularity deviation of the inner electrode after formation of the insulation layer can be small and the sensor can have a good detection accuracy. Further, since the circularity deviation of the inner electrode after formation of the insulation layer can be low, the accuracy in assembly of the sensor can be high. In the meantime, the difference in the thickness between the thickest portion and the thinnest portion of the insulation layer is preferably 200 μm or less.

Further, in the above-described electrostatic capacity type liquid state detecting sensor, the outer tubular electrode is preferably formed with at least one axial slit.

Such an axial slit enables liquid to circulate through the intervening space between the outer tubular electrode and the inner electrode and through the space outside the outer tubular electrode smoothly. By this, even when the liquid existing in the intervening space is mixed with a foreign matter, the foreign matter can be discharged through the slit to the outside, thereby preventing the foreign matter from being adhered to the insulation layer. Further, in case the liquid existing in the intervening space is cooled rapidly and frozen, a pressure rise caused by an increase in the volume of the liquid can be released to the outside of the outer tubular electrode through the slit, thus making it possible to prevent the outer tubular electrode from being deformed by the freezing of the liquid. In the meantime, a slit elongated axially of the outer tubular electrode enables the outer tubular electrode to have a good strength.

Further, in the above-described electrostatic capacity type liquid state detecting sensor, the outer tubular electrode is formed with the slit at an outer circumferential portion in the range from 3% to 10% of a whole outer circumference of the outer tubular electrode when observed in cross section.

Since in the electrostatic capacity type liquid state detecting sensor, the outer tubular electrode is formed with the slit at an outer circumferential portion that is 3% or more of the whole outer circumference of the outer tubular electrode, a rising pressure caused by an increase in the volume of liquid existing in the intervening space between the outer tubular electrode and the inner electrode can be released to the outside effectively. Further, since the outer tubular electrode is formed with the slit at an outer circumferential portion (circumferential width of the slit) that is 10% or less of a whole outer circumference of the outer tubular electrode, a solid matter such as a block of ice that is formed by liquid positioned outside the outer tubular electrode and frozen and that is sized so as to damage the insulation layer when brought into contact with the insulation layer is difficult to pass through the slit, thus making it possible to protect the insulation layer from being damaged effectively.

Further, in the above-described electrostatic capacity type liquid state detecting sensor, a circumferential width of the slit is 5 mm or less.

Since a circumferential width of the slit is determined to be 5 mm or less, it becomes possible to prevent a sold matter such as a block of ice formed by liquid frozen at the outside of the outer tubular electrode or the like that can damage the insulation layer from entering into the inside of the outer tubular electrode through the slit and thereby protect the insulation layer against such a solid matter effectively.

In the above-described electrostatic capacity type liquid state detecting sensor further including an insulation support member surrounding a rear end side of the inner electrode and a sealing member disposed between an inner surface of the insulation support member and an outer surface of the inner electrode to provide a seal therebetween, the liquid is electrically conductive and the inner electrode is formed with the insulation layer at an outer surface portion which extends from a front end thereof to a place where the sealing member and the inner electrode are joined.

In the electrostatic capacity type liquid state detecting sensor, the sealing member is disposed as described above for preventing the liquid from flowing out from the rear end side through an opening between the outer surface of the inner electrode and the inner surface of the insulation support member. However, in case the liquid is electrically conductive as urea water, forming the insulation layer only on an outer surface portion of the inner electrode that protrudes from a front end of the insulation support member causes a possibility that the sensor becomes unable to detect the liquid state correctly due to a short between the outer electrode and the inner electrode when the container is filled with electrically conductive liquid so as to allow the liquid to enter into the space between the inner surface of the insulation support member and the outer surface of the inner electrode. In contrast to this, in the electrostatic capacity type liquid state detecting sensor, the inner electrode is formed with the insulation layer with the above-described thickness limits at least at an outer surface portion which extends from a front end thereof to a place where the sealing member and the inner electrode are joined. By this, even when conductive liquid enters into the space between the inner surface of the insulation support member and the outer surface of the inner electrode, a short between the outer tubular electrode and the inner electrode can be prevented assuredly, thus making it possible to detect the liquid state with accuracy.

DESCRIPTION OF THE PREFERRED EMBODIMENT

Figure 1:
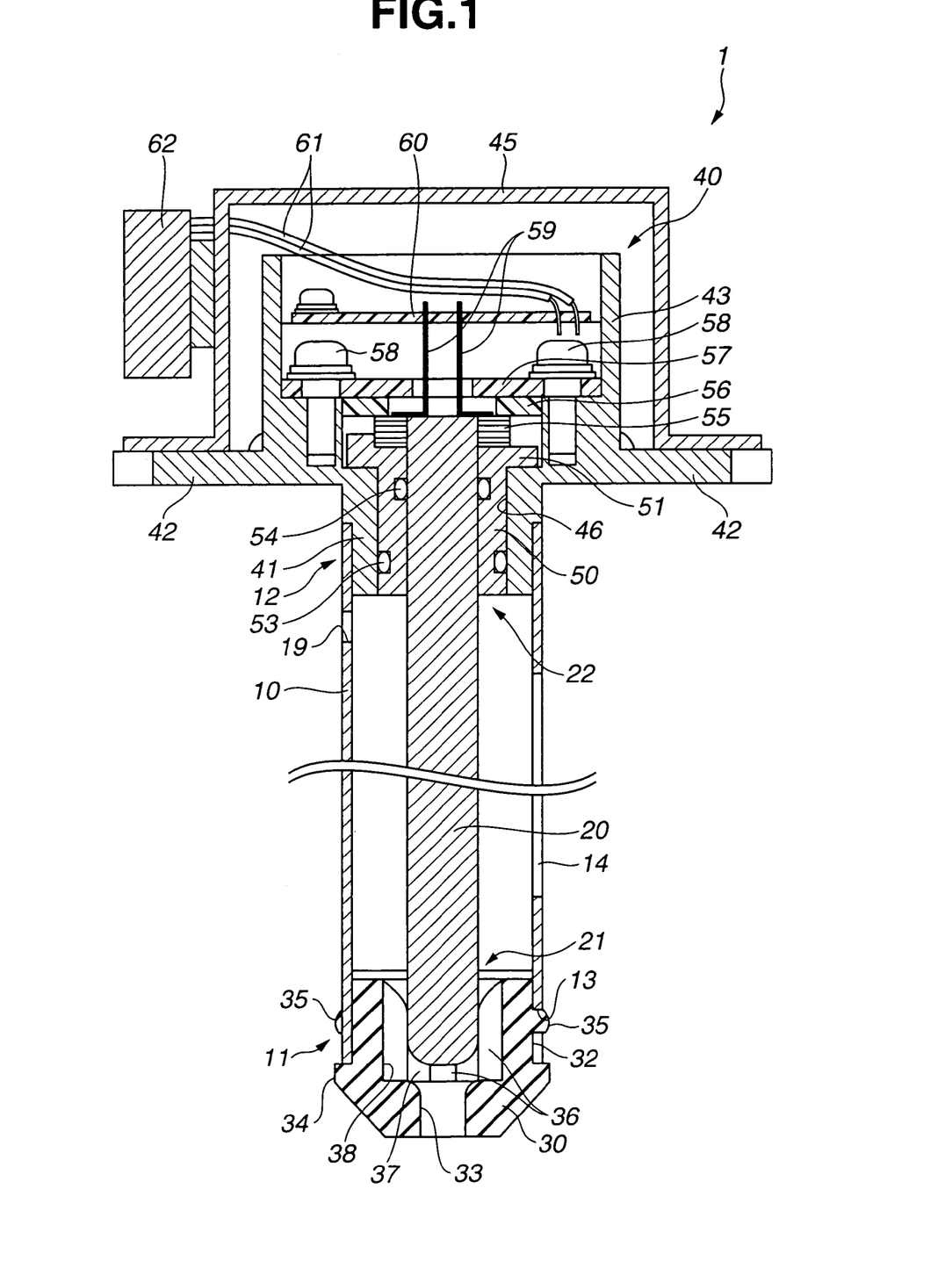
FIG. 1 is a longitudinal sectional view of an electrostatic capacity type liquid level sensor according to an embodiment of the present invention.

Referring first to FIG. 1, an electrostatic capacity type liquid state detecting sensor according to an embodiment of the present invention will be described by taking an electrostatic capacity type liquid level sensor 1 as an example.

The liquid level sensor 1 is installed on a tank or container (not shown) containing urea water that is used for reduction of nitrogen oxides (NOx) contained in the exhaust gases emitted from a diesel vehicle and is used for detecting the liquid state, i.e., for measuring the level of urea water in the container.

As shown in FIG. 1, the liquid level sensor 1 consists of an outer tubular electrode 10 that is hollow cylindrical, an inner electrode 20 disposed coaxially within the outer tubular electrode 10 and a base portion 40 that holds the outer tubular electrode 10 and the inner electrode 20 spaced apart from each other, i.e., in a non-contacting state.

The outer tubular electrode 10 is made of an electrically conductive metal and has a slender, hollow cylindrical shape. At a front end or lower end portion 11 of the outer tubular electrode 10 of the liquid level sensor 1 is provided a resilient support member or bushing 30 that is made of rubber and engaged with the front end portion 11 of the outer tubular electrode 10 (i.e., the end portion opposite to a base portion 40 of the outer tubular electrode 10). The bushing 30 has a hollow cylindrical body portion 32 and a flange or head portion 34 on one end side of the body portion 32. The head portion 34 prevents the bushing 30 from moving further into the outer tubular electrode 10 when the bushing 30 is installed on the outer tubular electrode 10. The body portion 32 has at an outer circumferential periphery thereof protrusions 35. The protrusions 35 are engaged with respective openings 13 provided to the front end portion 11 of the outer tubular electrode 10. That is, the outer tubular electrode 10 has at a position adjacent the front end thereof the openings 13. The protrusions 35, when engaged with the openings 13, prevent the bushing 30 from being removed or dropped off from the outer tubular electrode 10 while cooperating with the flange portion 34 to position the bushing 30 in place. The bushing 30 has at the body portion 32 a support hole 38 for supporting the front end portion of the inner electrode 20. At an inner circumferential periphery of the support hole 38 are provided a plurality of axial ribs 36 and a plurality of communication grooves 37 that are arranged alternately in the circumferential direction. Namely, the support hole 38 has at the inner circumferential periphery the communication grooves 37 that are arranged at predetermined circumferential intervals, and the communication grooves 37 are provided between adjacent two of the axial ribs 36. The front end portion 21 of the inner electrode 20 is positioned and held in place by the ribs 36 such that the inner electrode 20 and the outer tubular electrode 20 are prevented from being brought into contact with each other. By the ribs 36 that are abuttingly engaged with the inner electrode 20, i.e., by the resilient support member 30 that resiliently supports the inner electrode 20 on an inside of the outer tubular electrode 10, an insulation layer of the thickness less than 500 μm and not less than 100 μm, which is formed on the outer surface of the inner electrode 20 as will be described later, is assuredly prevented from being broken or damaged. The bushing 30 has at a bottom of the support hole 38 a communication hole 33 in communication with the communication grooves 37 so that fluid communication between the inside and the outside of the bushing 30 is established through the communication hole 33 and the communication grooves 37 between the adjacent ribs 36 even when the inner electrode 20 is in a state of being held by the ribs 36. The communication hole 33 and the communication grooves 37 thus constitute a liquid flow passage through which the liquid flows through the bushing 30 into the inside of the outer tubular electrode 10, i.e., a liquid flow passage that enables urea water contained in the container to be introduced into the intervening space between the outer tubular electrode 10 and the inner electrode 20.

The outer tubular electrode 10 has at the outer circumferential periphery a plurality of narrow slits 14 that are located on the same generating line as the opening 13, i.e., located circumferentially the same as the opening 13 and that are arranged at intervals along one generating line extending from the front end portion 11 of the outer tubular electrode 10 to the base portion 12 (the base portion 40 side end portion of the outer tubular electrode 10). Three sets of the slits 14 and the opening 13 are provided on three generating lines and arranged circumferentially at equal intervals on the outer circumferential periphery of the outer tubular electrode 10. By way of those slits 14, urea water contained in the container can flow smoothly between the above-described intervening space and the outside of the outer tubular electrode 10. Further, at the base end portion 12 of the outer tubular electrode 10 is formed an air vent 19 that is located on a generating line different from the generating lines on which the slits 14 are formed.

The outer tubular electrode 10 is engaged at the base end portion 12 with an outer circumferential periphery of an electrode support portion 41 of the sensor base 40 that is made of metal and fixedly attached thereto by welding. The base portion 40 serves as a support for fixing the liquid level sensor 1 to the container (not shown) containing urea water and has at a flange section 42 thereof holes (not shown) used for the fixing of the liquid level sensor 1. Further, on the side of the flange section 42 opposite to the electrode supporting section 41, the base portion 40 is formed with a housing section 43 for receiving therewithin a relaying circuit board 60 or the like that is used for electrically connecting the outer tubular electrode 10 and the inner electrode 20 with an outside circuit (not shown). In the meantime, the circuit board 60 is mounted on board support sections (not shown) protruding from four inner wall corners of the housing section 43. The circuit board 60 is electrically connected to the outside circuit by way of a connector 62 which is attached to a side of a cover 45 which is in turn fixedly attached to the flange section 42. The connector 62 has an outside connection terminal (not shown) that is electrically connected to the wiring of the circuit board 60 by means of distributing cables 61.

The electrode support section 41 of the base portion 40 has an opening 46 that extends therethrough and opens to the inside of the housing section 43. Within the opening 46 is fixedly disposed the inner electrode 20. The inner electrode 20 of this embodiment is a conductive metallic bar having a solid cylindrical shape and has a length nearly equal to that of the outer tubular electrode 10. The end portion of the inner electrode 20 on the front end portion 21 side (i.e., the lower side in FIG. 1 and the front end side of the liquid level sensor 1) is chamfered or rounded. On the outer circumferential surface of the inner electrode 20 is formed an insulation layer 23 (refer to FIG. 3) made of fluororesin such as PTFE, PFA and ETFE. The insulation layer 23 is a resin coating layer formed by applying fluororesin to the outer surface of the inner electrode 20 by dipping or electrostatic powder painting and by heat-treating the applied fluororesin. Further, on the base end portion 22 side (the upper side in FIG. 1) are provided a pipe guide 55 and an inner case or insulation support member 50 for fixedly attaching the inner electrode 20 to the base portion 40. The pipe guide 55 is an annular guide member joined to the end of the base end portion 22 of the inner electrode 20.

Further, the insulation support member 50 is a tubular resinous member for positioning and supporting the inner electrode 20 so that the inner electrode 20 and the outer tubular electrode 10 are assuredly insulated from each other. The insulation support member 50 is engaged at a front end side in the opening 46 of the electrode support section 41. The insulation support member 50 has a radially outward flange 51. At the time of engagement with the electrode support section 41, the insulation support member 50 is inserted from the housing section 43 side into the opening 46 of the electrode support section 41. The flange 51 is brought into abutting engagement with the bottom of the housing section 43 and thereby prevents the insulation support member 50 to pass through the electrode support section 41. The inner electrode 20 is also inserted from the housing section 43 side into the inside of the insulation support member 50 and prevented from passing through the insulation support member 50 by means of the pipe guide 55 that is abuttingly engaged with the flange 51.

Further, the insulation support member 50 has at the inner and outer circumferential peripheries thereof a first sealing member or O-ring 53 and a second sealing member or O-ring 54, respectively. The first O-ring 53 provides a seal between the outer circumferential periphery of the insulation support member 50 and the opening 46 of the base portion 40. The second O-ring 54 provides a seal between the inner circumferential periphery of the insulation support member 50 and the outer circumferential periphery of the base end portion 22 of the inner electrode 20. This prevents the inside and the outside of the container from being communicated through the housing section 43 for thereby attaining a seal therebetween when the liquid level sensor 1 is installed on the container (not shown). In the meantime, a rubber member in the form of a plate, though not shown, is fittingly installed on the flange section 42 of the base portion 40 at the time of installation of the liquid level sensor 1 on the container, similarly to the first O-ring 53 and the second O-ring 54, so as to attain a seal between the inside and the outside of the container.

At the time of attachment of the inner electrode 20 to the base portion 40, the pipe guide 55 is pressed against the flange 51 of the insulation support member 50 by means of two pressure plates 56, 57. The pressure plate 57 is fixed by means of screws 58 within the housing section 43 while being held in a state of pushing the pipe guide 55 and interposing the pressure plate 56 between the pipe guide 55 and the pressure plate 57. By this, the inner electrode 20 connected to the pipe guide 55 is fixedly attached to the electrode support section 41. The pressure plates 56, 57 have central holes (no numeral) through which electrode taking-out lead wires 59 of the inner electrode 20 are passed for connection to the circuit board 60. Though not shown, a ground side electrode of the circuit board 60 is connected to the base portion 40, so that the outer tubular electrode 10 is electrically connected to the ground side.

Figure 2:
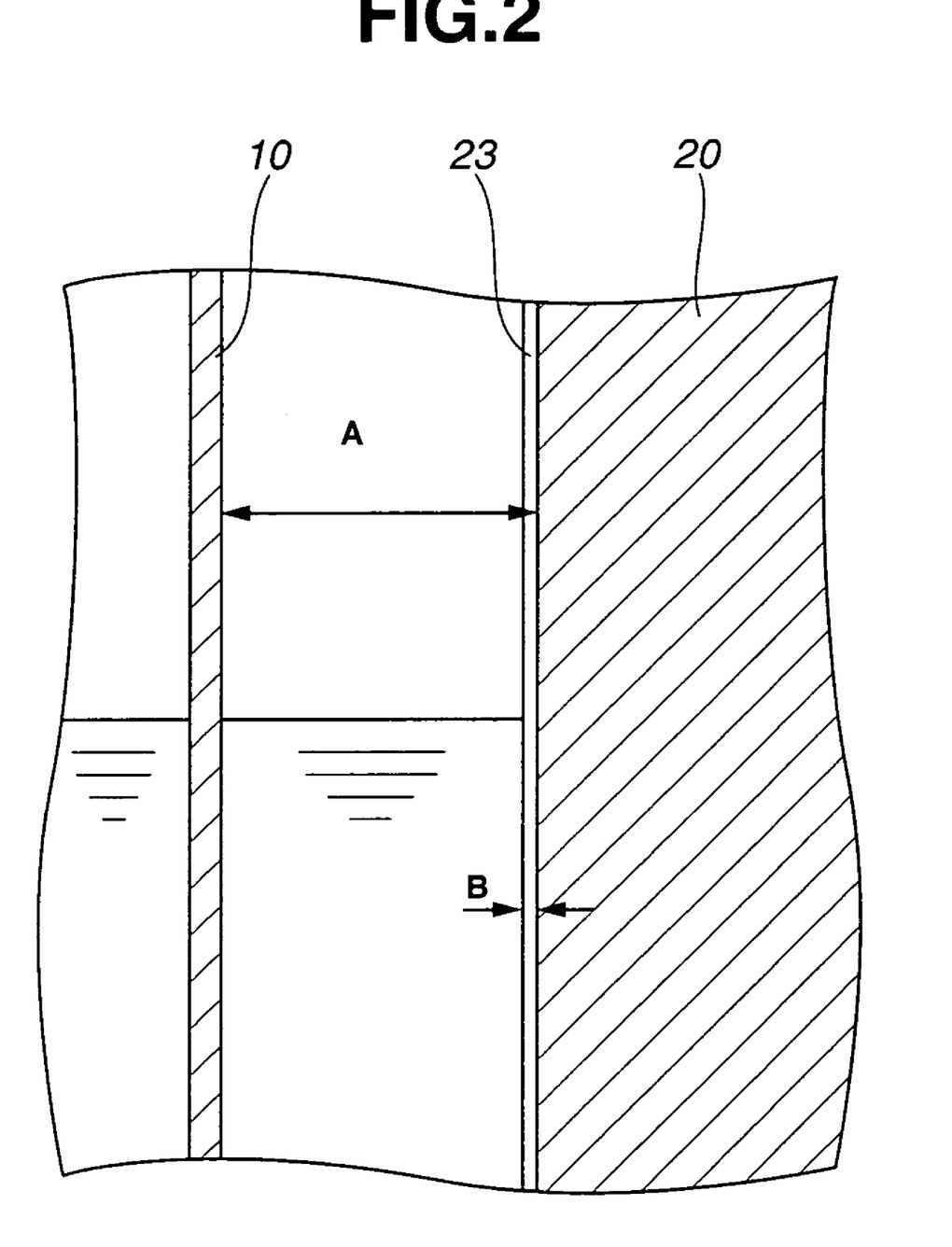
FIG. 2 is an enlarged sectional view of a portion of the liquid level sensor of FIG. 1 and shows a water level of urea water filled in a space between an outer tubular electrode and an inner electrode of the liquid level sensor of FIG. 1.

Then, the theory of detecting the state of liquid such as water level (level of urea water in this embodiment) by means of the liquid level sensor 1 of this embodiment will be described with reference to FIG. 2. FIG. 2 is an enlarged sectional view of a portion of the liquid level sensor 1 that is located adjacent the level of urea water filled in the space between the outer tubular electrode 10 and the inner electrode 20. The liquid level sensor 1 is attached to the container (not shown) containing urea water so as to extend axially along the up and down direction of the level of urea water. By detecting the electrostatic capacity between the outer tubular electrode 10 and the inner electrode 20, it becomes possible to detect how high is the level of urea water existing between the outer tubular electrode 10 and the inner electrode 20. This, as is well known, depends on the fact that the electrostatic capacity between two points of different potentials is inversely proportional to the distance between the two points.

Namely, as shown in FIG. 2, the distance "A" indicates the distance at which a potential difference is caused at an intervening space portion not filled with urea water, i.e., the distance "A" is equal to the sum of the thickness of the air layer between the outer tubular electrode 10 and the inner electrode 20 and the thickness of the insulation layer 23. On the other hand, the distance "B" indicates the distance at which a potential difference is caused at an intervening space portion filled with urea water, i.e., the distance "B" is equal to the thickness of the insulation layer 23 since urea water is electrically conductive so that the outer tubular electrode 10 and urea water are equal in the potential. Namely, the intervening space portion filled with urea water is smaller in the distance at which the potential difference is caused and is therefore larger in the electrostatic capacity than the intervening space portion not filled with urea water. For this reason, when a voltage is applied across the intervening space, the rate of the space portion of the distance "B" that causes a larger electrostatic capacity increases as the space portion filled with urea water increases. In this connection, as is well known, the electrostatic capacity is proportional to the area of the opposing portions that are different in the potential, so that the entire electrostatic capacity that is detected by the liquid level sensor 1 increases as the level of urea water becomes higher.

In such measurement of the level of liquid, a larger electrostatic capacity can be attained as the thickness of the insulation layer 23 formed on the outer surface of the inner electrode 20 becomes smaller. However, since the insulation layer 23 made of fluororesin is easily damaged when subjected to an impact, the thickness of the insulation layer 23 in this embodiment is determined to be 100 μm or more (preferably, 150 μm or more). By this, the damage-resisting property of the insulation layer 23 becomes higher, so that even in the case the surface of the insulation layer 23 is subjected to an impact and damaged, it becomes possible to prevent the insulation layer from being broken to expose the surface of the inner electrode 20 to the outside and thereby prevent the insulation property of the inner electrode 20 from being deteriorated.

Further, as described above, the insulation layer 23 is formed by applying fluororesin to the outer surface of the inner electrode 20 by dipping or electrostatic power painting and heat-treating the applied or painted fluororesin. The thickness of an insulation layer that can be formed by one processing for forming the insulation layer 23 is generally 50 μm or so. Thus, on an insulation layer having been formed is further formed an insulation layer. Namely, several times of processings for forming an insulation layer on the surface of the inner electrode 20 are performed. Thus, even if the insulation layer formed by one processing has a portion that is not continuous, the portion that is not continuous is buried by an insulation material at a later processing since forming of the insulation layer is repeated several times. If the thickness of the insulation layer 23 is 100 μm or more (preferably 150 μm or more), the processing for forming the insulation layer is performed at least two times, it becomes possible to prevent unintended occurrence of the insulation layer having a portion that is not continuous and prevent occurrence of defective insulation.

Further, in this embodiment, the thickness of the insulation layer 23 is determined to be less than 500 μm. By determining the thickness of the insulation layer 23 to be less than 500 μm, the floating capacity can be sufficiently smaller as compared with the electrostatic capacity to be measured and therefore can be regarded as noise to be ignored, thus not lowering the detection accuracy of the sensor.

Further, in this embodiment, the insulation layer 23 of the thickness with the above-described limits is formed continuously at least at a portion of the outer surface of the inner electrode 20, which portion extends from the front end to the joining section between the second O-ring 54 and the inner electrode 20. By this, even if urea water enters into the space between the inner circumferential surface of the insulation support member 50 and the outer circumferential surface of the inner electrode 20 when the container is filled with electrically conductive urea water, it becomes possible to prevent occurrence of a short between the outer tubular electrode 10 and the inner electrode 20 and therefore it becomes possible to detect the level of urea water accurately.

Figure 3:
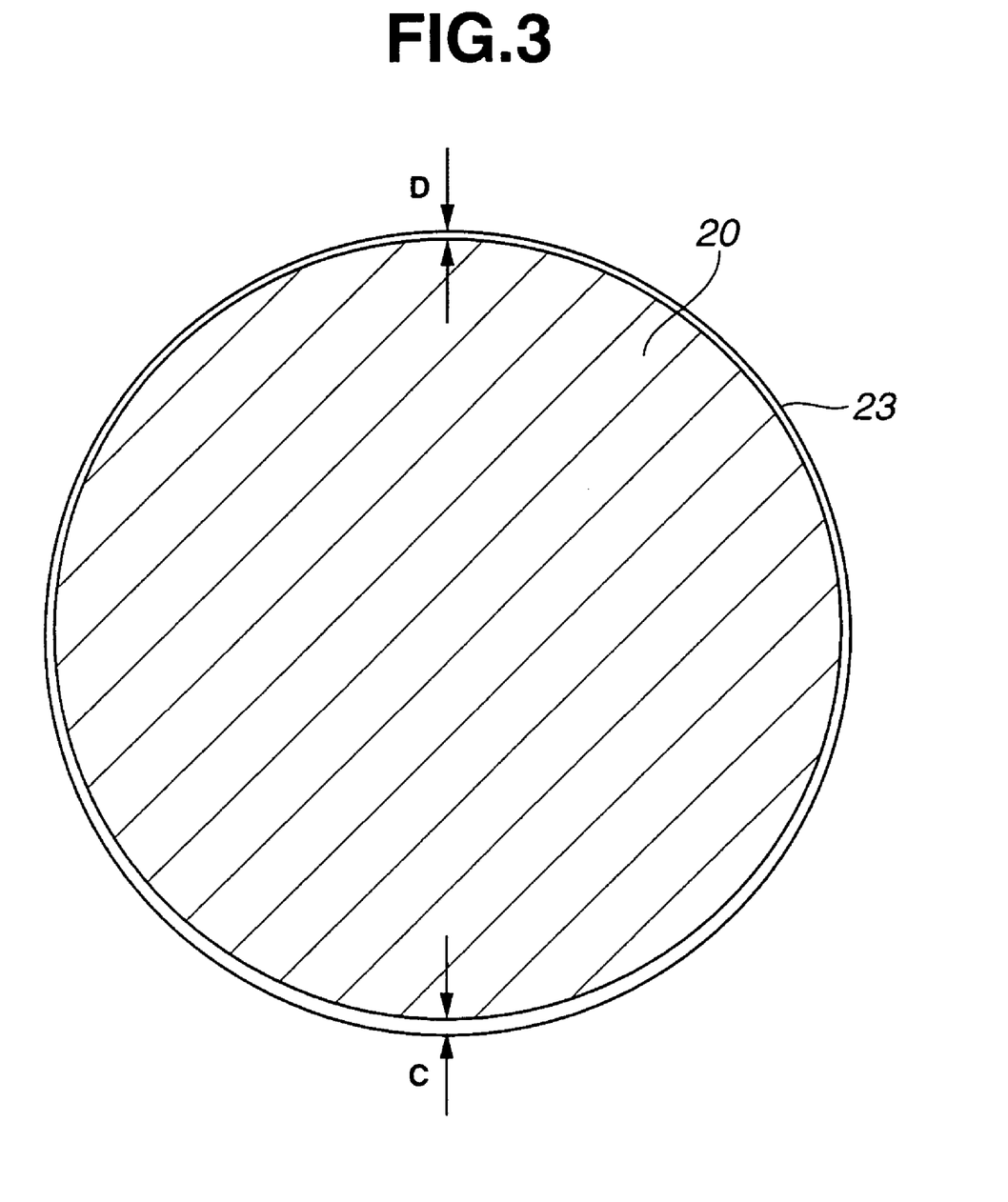
FIG. 3 is a cross sectional view of the inner electrode.

In the meantime, since the thickness of the insulation layer 23 that can be formed by one processing is about 50 μm as described above, setting the thickness of the insulation layer 23 at a value close to 500 μm requires an increased number of processings to be repeated for forming the insulation layer. In such a case, the insulation layer 23 may possibly become irregular in thickness, i.e., may cause thickness irregularities due to the self-weight of fluororesin at the time of curing. Further, depending upon the conditions for forming the insulation layer, the insulation layer 23 has a possibility of causing the above-described surface irregularities. Thus, in this embodiment, as shown in FIG. 3, the difference (hereinafter referred to as "circularity deviation (mm in unit)") between the thickness of the thickest portion (indicated by C in the figure) and the thinnest portion (indicated by D in the figure) of the insulation layer 23 is determined to be 0.3 mm (300 μm) or less with respect to a section crossing the center axis of the inner electrode 20 at right angles, i.e., when observed in cross section. Namely, if the circularity deviation is 0 (zero) mm, the outer circumferential periphery of the insulation layer, when observed in cross section, is shaped to be truly circular. If the inner circumferential periphery of the insulation support member 50 on which the inner electrode 20 is supported by way of the electrode support section 41 is formed nearly truly circular and the above-described cross section of the inner electrode 20 is closer to a true circle, assembly of the sensor including the inner electrode 20 can be attained more accurately and the seal between insulation support member 50 and the inner electrode 20 by means of the O-ring 54 can be improved. Accordingly, determining the circularity deviation to be 0.3 mm (300 μm) or less and thereby making the insulation layer 23 have an outer circumferential shape that is close to a true circle is preferable from the accuracy in assembly of the sensor and from the point of view of improving the detection accuracy of the sensor.

Figure 4:
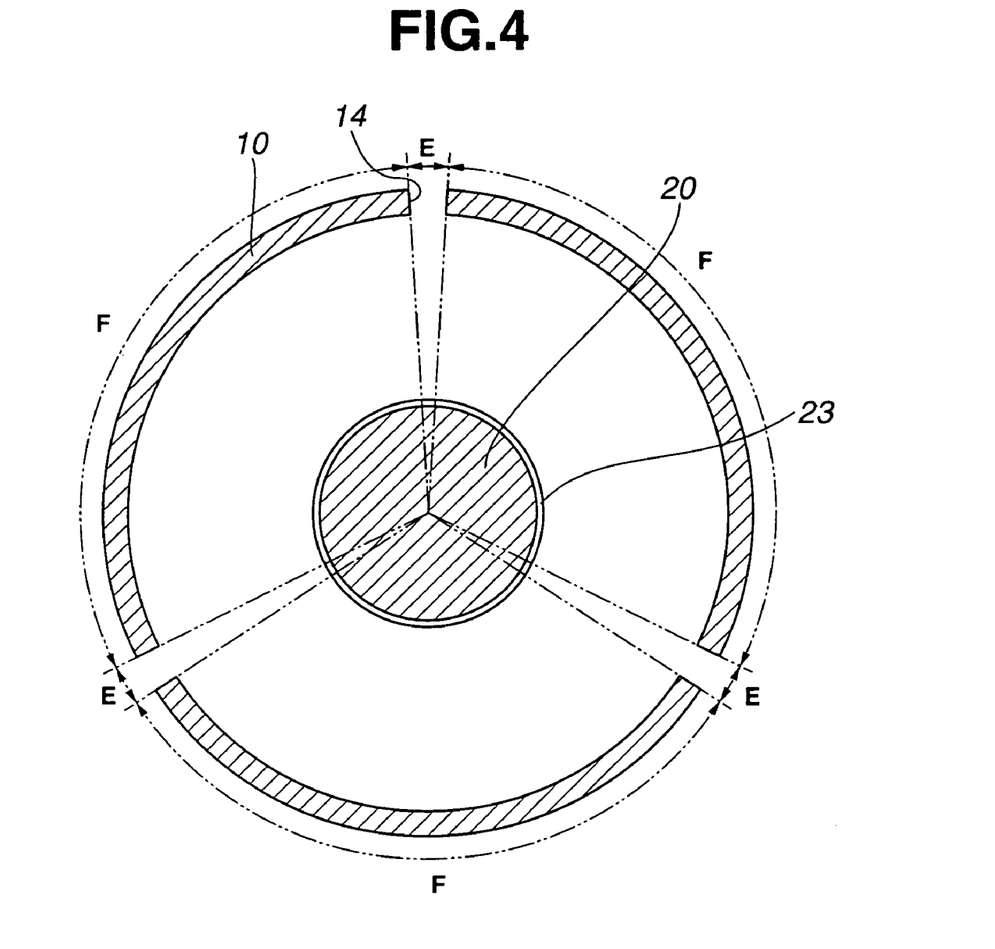
FIG. 4 is a cross sectional view of the outer tubular electrode and shows the positions of slits thereof.

The insulation layer 23 that is formed thin as described above has a possibility of loosing the insulation ability due to damage or the like in use of the sensor. For this reason, in the liquid level sensor 1 of this embodiment, limits to the width of the slit (width of opening) 14 formed in the outer tubular electrode 10 are set so that even when a solid matter such as a block of ice is present in urea water, it does not enter into the space between the outer tubular electrode 10 and the inner electrode 20. Hereinafter, with reference to FIG. 4, description will be made to the width of the slit 14. FIG. 4 shows the positions at which the slits 14 are formed in the outer tubular electrode 10 with respect to a section crossing the center axis of the outer tubular electrode 10 at right angles, i.e., when observed in cross section of the outer tubular electrode 10.

As shown in FIG. 4, the outer tubular electrode 10 is formed with the slits 14 that are respectively positioned on three generating lines spaced circumferentially at equal intervals. In FIG. 4, the circumferential width of the slit 14 when observed in cross section of the outer tubular electrode 10 is indicated by "E". Similarly, the circumferential width of the portion where the slit 14 is not formed is indicated by "F". Namely, the sum of the widths "E" and the widths "F" is the whole outer circumference of the outer tubular electrode 10.

In this embodiment, the sum of the widths "E" of the slits 14 is determined to be 10% or less of the whole outer circumference (i.e., the sum of the widths "E" and the widths "F") of the outer tubular electrode 10. By so determining the widths of the slits 14, if impurities or solid matters such as blocks of frozen urea water are contained in urea water, such solid matters become difficult to pass through the slits 14, thus making it possible to protect the insulation layer 23 from the solid matters and prevent the same from being damaged. In the meantime, even if the width "E" of the slit 14 is less than 10% of the whole outer circumference of the outer electrode 10, there may occur such a case in which a small solid matter passes through the slit 14. However, even if the solid matter that can pass through the slit 14 strikes against the insulation layer 23 of the inner electrode 20, its mass is not large enough to damage the insulation layer 23 and therefore it is difficult for such a solid matter to cause an influence on the insulation ability.

In the meantime, in this embodiment, the circumferential with "E" of the slit 14 is set at 2.5 mm. By determining the circumferential width of each slit 14 to be 5 mm or less, it becomes possible to prevent a solid matter such as a block of ice that is formed from frozen urea water at the outside of the outer tubular electrode 10 and that is large enough to damage the insulation layer 23 from entering into the inside of the outer tubular electrode 10 through the slits 14. Accordingly, protection of the insulation layer 23 can be attained effectively.

Further, the slit 14 in the liquid level sensor 1 in this embodiment is formed so as not to cause the outer tubular electrode 10 to be deformed due to a rise in the pressure that is accompanied by freezing of urea water existing in the intervening space. More specifically, if the urea water existing in the intervening space is cooled rapidly, there may occur such a case in which urea water in the intervening space starts freezing at both of the front end portion 11 side and the basic end portion 12 side of the outer tubular electrode 10. As a result, there occurs a rise of pressure that is caused by the freezing and is directed toward the intermediate side of urea water existing in the intervening space. However, since circulation of urea water between the inside and the outside of the outer tubular electrode 10 is attained by the slits 14, the above-described pressure rise can be resultantly released to the outside. To obtain such an effect, it is preferable that the sum of the widths "E" of the slits 14 is 3% or more of the whole outer circumference of the outer tubular electrode 10 (the sum of the widths "E" and widths "F").

In this manner, the liquid level sensor 1 of this embodiment is configured so as to be capable of preventing an ill effect (damage caused by striking of solid matter) that is caused when the insulation layer 23 is made thinner in order that the insulation layer 23 can be made thinner. By defining the thickness of the insulation layer 23 as described above at the time of formation of the insulation layer 23 that is thin, an insulation defect is prevented and the liquid level sensor 1 having a good detection accuracy is realized. In order to recognize the effect obtained by defining the thickness of the insulation layer as described above, the following four evaluation tests were conducted.

[Evaluation Test I]

An evaluation test for the insulation ability in relation to the thickness of the insulation layer was conducted. The evaluation test was conducted under the following conditions. As the inner electrode is used a circular metal tube of 493.5 mm in overall length, 10 mm in outer diameter and 1.5 mm in thickness. SUS304 is used for the material of the metal tube. On the outer surface of the inner electrode is formed a coating of PFA over the length of 485.5 mm and is thereby formed an insulation layer. The coating was performed by electrostatic powder painting and it is determined that paining, drying, fixing by heat and cooling constitute one cycle. In this instance, the control for forming the insulation layers of the thickness of less than 100 μm was performed by controlling a painting time, the control for forming the insulation layers of the thickness of 100 μm or more was performed by varying the number of the cycles.

Then, each of examples with the insulation layers of 50, 75, 100, 125, 150 and 200 μm thick was prepared by 20 in number and all of the examples were subjected to an insulation test. A voltage (1000V) was applied across the inner circumferential periphery of the inner electrode and an electrode mounted on the insulation layer and absorbent cotton wetted by electrically conductive liquid was let to run on the insulation layer. Under this condition, it was recognized whether the insulation was provided between the inner electrode and the electrode mounted on the insulation layer. Then, with respect to each kind of examples with the insulation layers of the same thickness, it was judged whether the number of defective examples that were defective in insulation was less than 10% of the total number of examples, i.e., twenty. When the number of defective examples was less than 10% (in other words, more than 90% of examples was judged good), the example of that kind was judged good.

Figure 5:
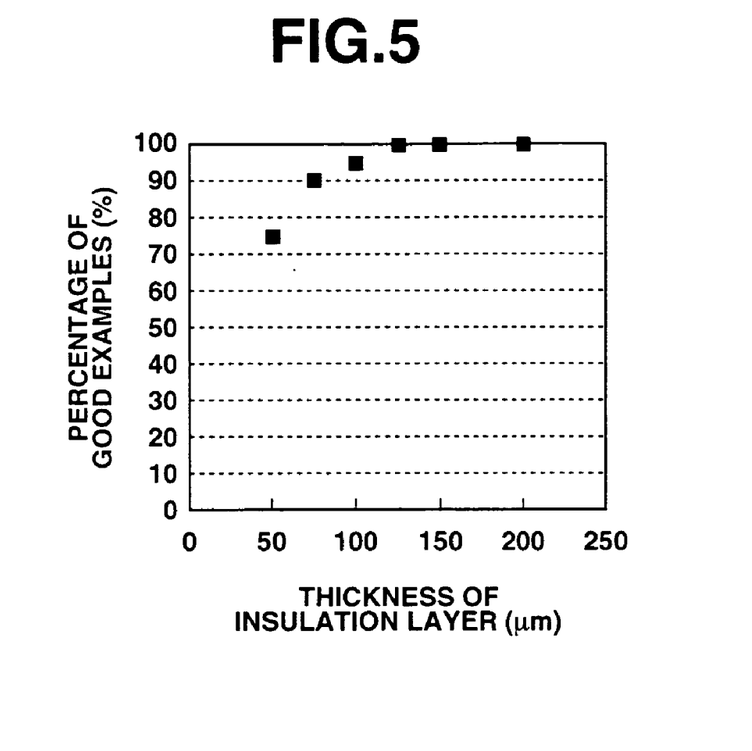
FIG. 5 is a graph showing the result of an evaluation test for an insulation ability in relation to the thickness of an insulation layer.

As shown in FIG. 5, the percentages of good examples when the insulation layers were 50 μm and 75 μm thick were 75% and 90%, respectively. Further, the percentage of good examples when the insulation layer was 100 μm was 95%. Further, the percentages of good examples when the insulation layers were 125 μm, 150 μm and 200 μm thick were all 100%. From this result, it is revealed that when the insulation layer is 100 μm or more thick a sensor that is defective in insulation is hard to be produced and further that if the insulation layer is 125 μm or more thick, a sensor that is defective in insulation is not produced. The defective insulation is mainly due to discontinuity of the insulation layer that was caused at the time of formation of the insulation layer, and the rate of occurrence of the discontinuity decreases with increase in the thickness of the insulation layer. Further, an increased number of cycles for coating of PFA enables the insulation to be attained more assuredly since, for example, if the discontinuity of the insulation layer is caused at the initial cycle, the discontinuity will be buried and eliminated at the next cycle, thus attaining the insulation. For this reason, it is found that the insulation layer is preferably 100 μm or more thick and more preferably 125 μm or more thick.

[Evaluation Test II]

An evaluation test for whether a defect of insulation is caused by a damage or the like defect of the insulation layer was conducted. The inner electrode used in this evaluation test was the same as that used in the evaluation test I. Of the examples with the insulation layers of 50, 75, 100, 125 and 200 μm thick, 20 examples that were judged good by the test similar to the evaluation test I were prepared for each thickness. Then, all the examples were subjected to an impact test. Namely, a block of SUS303 is placed on a test board or desk, and an example is held vertically and then fell down toward the block of SUS303. This falling of the example is performed by natural falling and the example is made to strike against the block of SUS303 at a portion that is spaced from the upper end of the example held vertically by ⅓ of the total length. This falling was performed three times repeatedly per each example. Then, the same insulation test as that in the evaluation test I was conducted, and the rate of the number of examples that became defective in insulation and judged not good (defective) to the total number of examples of each thickness, i.e., 20 was searched and the percentage defective was examined.

Figure 6:
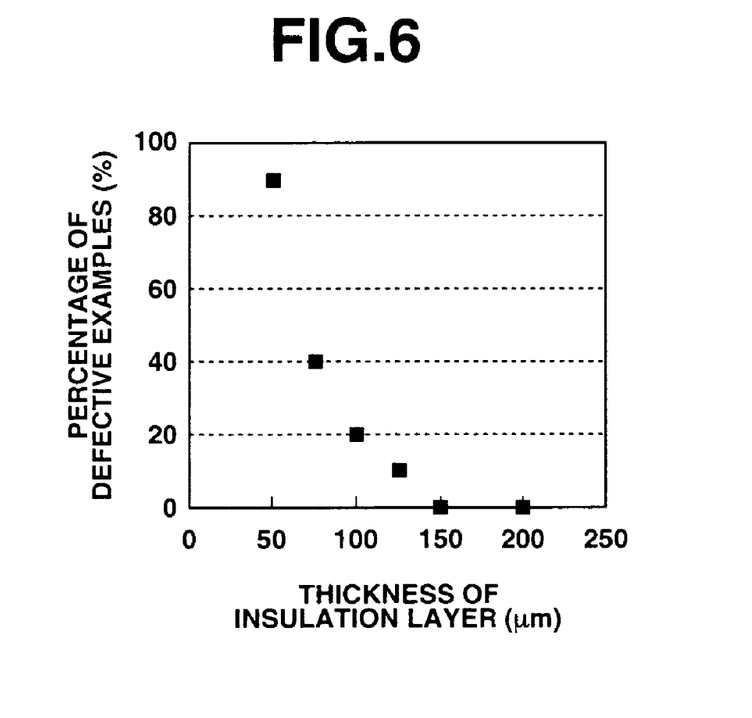
FIG. 6 is a graph showing the result of an evaluation test for whether a defect of insulation is caused by a damage of an insulation layer.

As shown in FIG. 6, the percentages of defective examples when the insulation layers were 50 μm and 75 μm thick were 90% and 40%, respectively. Further, when the percentages of defective examples when the insulation layers were 100 μm and 125 μm thick were 20% and 10%, respectively. When the percentages of defective examples when the insulation layers were 15 μm and 200 μm thick were all 0%. From this result, it is found that when the insulation layer is 100 μm or more thick, the percentage of defective examples can be held at the minimum or less and that if the insulation layer is 150 μm or more thick the insulation can be maintained since the surface of the inner electrode is not exposed even when the insulation layer is subjected to an impact and damaged.

[Evaluation Test III]

An evaluation test for the electrostatic capacity in relation to the thickness of the insulation layer was conducted. The inner electrode used in this evaluation test was the same as the evaluation test I, and examples with the insulation layers of 100, 200, 300, 350, 450, 500, 600 and 700 μm were prepared and subjected to the same test as the evaluation test I. Of those examples, the examples that were judged good were used for this evaluation test. By using those inner electrodes, electrostatic capacity type liquid state detecting sensors generally similar to the above-described embodiment were prepared (in the meantime, as the outer electrode was used a metal tube of 30 mm in outer diameter and 1.0 mm thick) and attached to a container filled maximumly with urea water to measure the electrostatic capacity.

Figure 7:
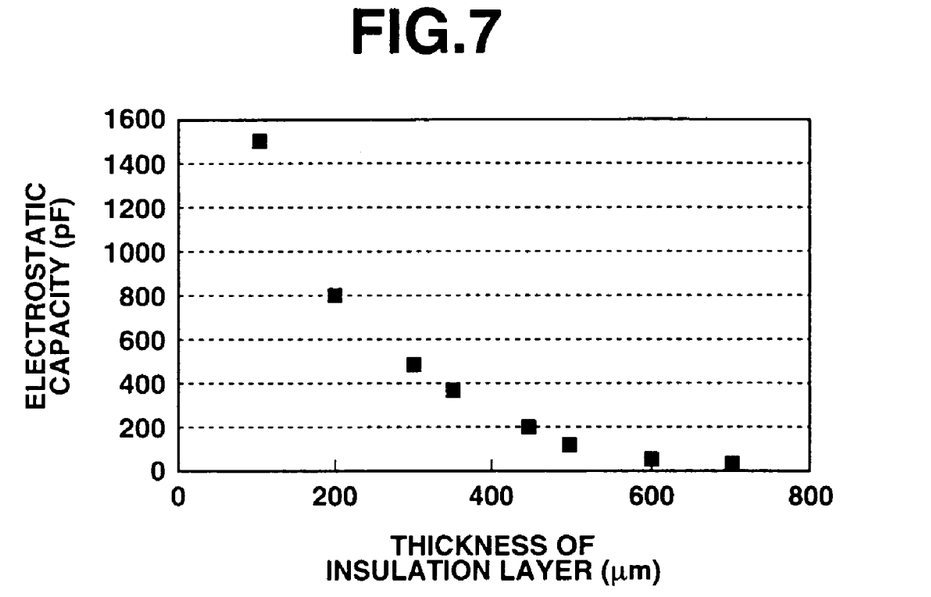
FIG. 7 is a graph showing the result of an evaluation test for the electrostatic capacity in relation to the thickness of insulation layer.

As shown in FIG. 7, the electrostatic capacities between the outer tubular electrode and the inner electrode when the insulation layers were 100, 200, 300, 350, 450, 500, 600 and 700 μm thick were 1500, 800, 500, 380, 210, 130, 70 and 50 pF, respectively. The electrostatic capacity that is measured when the container is maximumly filled with urea water is a maximum value of the electrostatic capacity that can be measured by the liquid state detecting sensor. As the maximum value of the electrostatic becomes larger, more sufficient measurement of the level of liquid can be attained even if fine measurement of the electrostatic capacity between 0 (zero) and the maximum value cannot be attained. Namely, depending upon the electrostatic capacity, a circuit that is low in resolving power and low in price can be used as a circuit for detecting the level of liquid. From the result of the evaluation test, it is found that if the insulation layer is less than 500 μm thick a circuit of low price and having a necessary resolving power can be used for the sensor with the maximum value of the electrostatic capacity being 130 pF or more.

[Evaluation Test IV]

An evaluation test for the circularity deviation in relation to the thickness of the insulation layer was conducted. The inner electrode used in this evaluation test is the same as the evaluation test I and the circularity deviations of the examples with the insulation layers of 100, 200, 300, 350, 450, 500, 550 and 700 μm thick were measured.

Figure 8:
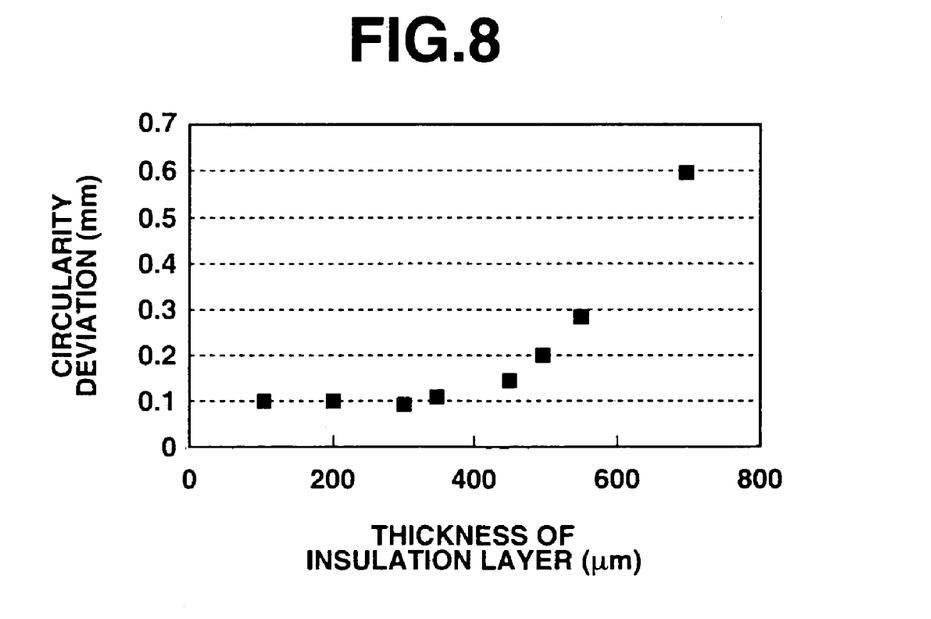
FIG. 8 is a graph showing the result of an evaluation test for the circularity deviation of the inner electrode in relation to the thickness of insulation layer.

As shown in FIG. 8, the circularity deviations of the inner electrodes with the insulation layers of 100, 200, 300, 350, 450, 500, 550 and 700 μm thick were 0.10, 0.10, 0.10, 0.11, 0.15, 0.20, 0.28 and 0.60 mm, respectively. From the result of the evaluation test, it was recognized that if the thickness of the insulation layer was less than 500 μm, the circularity deviation could be less than 0.3 mm (300 μm) and the accuracy in assembly of the sensor could be good. In the meantime, from the result of the evaluation test IV, the circularity deviation was less than 300 μm when the thickness of the insulation layer was less than 500 μm, but depending upon the condition at the time of formation of the insulation layer (specifically, depending upon the condition at the time of electrostatic powder painting), there occurred a case in which the circularity deviation was larger than 0.15 mm even when the thickness of the insulation layer was 450 μm. However, so long as the thickness of the insulation layer is less than 500 μm and not less than 100 μm, the circularity deviation is maintained 300 μm or less, which is allowable from the point of view of the accuracy in assembly of the sensor.

The entire contents of Japanese Patent Applications P2004-186042 (filed Jun. 24, 2004) are incorporated herein by reference.

Figure 9:
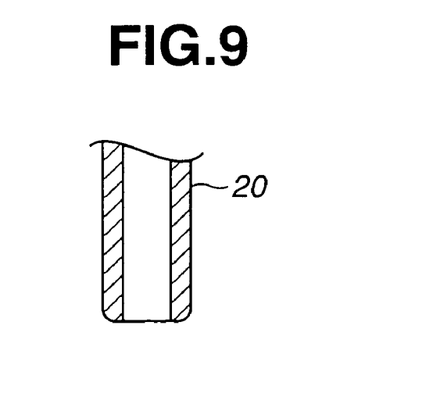
FIG. 9 is a fragmentary sectional view of a modification of the inner electrode of the liquid level sensor of FIG. 1.

Although the invention has been described above by reference to a certain embodiment of the invention, the invention is not limited to the embodiment described above. Modifications and variations of the embodiment described above will occur to those skilled in the art, in light of the above teachings. For example, while the inner electrode has been described and shown as being in the form of a solid cylinder, this is not for the purpose of limitation and it can be in the form of a hollow cylinder as shown in FIG. 9. Further, the inner electrode is not necessarily cylindrical but it could be in the form of a rectangular or square rod or in the form of a square or rectangular tube. Further, the outer tubular electrode 10 is not limited to a cylindrical tube but could be in the form of a square or rectangular tube. Further, the liquid state to be detected is not limited to a water level (liquid level) but can be, for example, the density of liquid, the degree of deterioration, the mixing degree of foreign matters. Further, while the insulation layers 23 formed on the inner electrode 20 in this embodiment has been described as being made of fluororesin, this is not for the purpose of limitation but it will do to select a suitable material that is hard to corrode in accordance with the characteristics (e.g., oxidation and reduction property) of the liquid the state of which is to be detected. In the meantime, while the insulation layer has been described as being formed by dipping or electrostatic powder painting, it can be formed by using an insulation tube if there is not formed any air layer between the inner electrode and the insulation tube. However, it is preferable to form the insulation layer by resin coating as in this embodiment. Further, while in this embodiment the slits 14 have been described as being formed on three different generating lines on the outer surface of the outer tubular electrode 10, the number of the generating lines on which the slits 14 are formed is not limited to three but can one, two, four or more. Further, while the slits 14 have been described as being formed on one generating line at intervals, they can be formed without intervals, i.e., into one slit. Further, in case a plurality of slits are formed axially of the outer tubular electrode 10, it is not necessitated to form the slits on one generating line but on a spiral or zigzag line. The scope of the invention is defined with reference to the following claims.

What is claimed is:

1. An electrostatic capacity type liquid state detecting sensor comprising:
    an outer tubular electrode; and
    an inner electrode disposed within the outer tubular electrode and having an insulation layer at an outer surface portion to be brought into contact with liquid contained in a container for detection of a state of the liquid;
    wherein the thickness of the insulation layer is less than 500 μm and not less than 100 μm, and
    wherein the outer tubular electrode is formed with at least one slit at an outer circumferential portion in the range from 3% to 10% of a whole outer circumference of the outer tubular electrode when observed in cross section.

2. An electrostatic capacity type liquid state detecting sensor according to claim 1, wherein the thickness of the insulation layer is less than 500 μm and not less than 150 μm.

3. An electrostatic capacity type liquid state detecting sensor according to claim 1, wherein the inner electrode is in the form of a solid cylinder, and wherein the difference in the thickness between a thickest portion and a thinnest portion of the insulation layer is 300 μm or less when observed in cross section.

4. An electrostatic capacity type liquid state detecting sensor according to claim 1, wherein the inner electrode is in the form of a hollow cylinder, and wherein the difference in the thickness between a thickest portion and a thinnest portion of the insulation layer is 300 μm or less when observed in cross section.

5. An electrostatic capacity type liquid state detecting sensor according to claim 1, wherein a circumferential width of the slit is 5 mm or less.

6. An electrostatic capacity type liquid state detecting sensor according to claim 1, further comprising an insulation support member surrounding a rear end side of the inner electrode and a sealing member disposed between an inner surface of the insulation support member and an outer surface of the inner electrode to provide a seal therebetween, wherein the liquid is electrically conductive and wherein the inner electrode is formed with the insulation layer at an outer surface portion which extends axially from a front end thereof to a place where the sealing member and the inner electrode are joined.

7. An electrostatic capacity type liquid state detecting sensor according to claim 6, wherein the liquid is urea water.

8. An electrostatic capacity type liquid state detecting sensor according to claim 1, wherein the outer tubular electrode and the inner electrode are disposed vertically so as to define therebetween a space which extends vertically and in which the liquid is introduced.

9. An electrostatic capacity type liquid state detecting sensor according to claim 1,
wherein the thickness of the insulation layer is less than 500 μm and not less than 100 μm, and
wherein the insulation layer is made of fluororesin.

10. An electrostatic capacity type liquid state detecting sensor according to claim 1,
wherein the outer tubular electrode is formed with at least one axial slit, and
wherein the outer tubular electrode is formed at a base end portion with an air vent.

11. An electrostatic capacity type liquid state detecting sensor according to claim 1, wherein the slit is an axial slit.

12. An electrostatic capacity type liquid state detecting sensor comprising:
an outer tubular electrode;
an inner electrode disposed within the outer tubular electrode and having an insulation layer at an outer surface portion to be brought into contact with liquid contained in a container for detection of a state of the liquid; and
a resilient support member interposed between the inner electrode and the outer tubular electrode for resiliently supporting the inner electrode on an inside of the outer tubular electrode,
wherein the thickness of the insulation layer is less than 500 μm and not less than 100 μm, and
wherein the resilient support member includes a support hole for supporting the inner electrode, the support hole having at an inner circumferential periphery a plurality of ribs arranged at predetermined circumferential intervals and abuttingly engaged with the inner electrode.

13. An electrostatic capacity type liquid state detecting sensor according to claim 12, wherein the resilient support member includes a communication hole at a bottom of the support hole and communication grooves between adjacent two of the ribs, the communication hole and the communication grooves constituting a liquid flow passage through which the liquid flows through the resilient support member into an inside of the outer tubular electrode.

14. An electrostatic capacity type liquid state detecting sensor according to claim 13, wherein the outer tubular electrode has at a position adjacent a front end thereof an opening, and wherein the resilient support member has at an outer circumferential periphery thereof a protrusion that is engaged with the opening of outer tubular electrode.

* * * * *